United States Patent [19]

Leber et al.

[11] Patent Number: 5,513,238
[45] Date of Patent: Apr. 30, 1996

[54] AUTOMATIC PLANNING FOR RADIATION DOSIMETRY

[75] Inventors: Zachary H. Leber, Cambridge; Hanne M. Kooy; Hsiao-Ming Lu, both of Newton, all of Mass.

[73] Assignee: Radionics, Inc., Burlington, Mass.

[21] Appl. No.: 321,298

[22] Filed: Oct. 11, 1994

[51] Int. Cl.$^6$ .................................................. A61N 5/10
[52] U.S. Cl. ....................................... 378/65; 364/413.26
[58] Field of Search .................... 378/64, 65; 364/413.26

[56]   References Cited

U.S. PATENT DOCUMENTS 5,291,404   3/1994   Kurokawa et al. ................ 364/413.26
5,317,616   5/1994   Swerdloff et al. ....................... 378/65

Primary Examiner—David P. Porta
Assistant Examiner—David Vernon Bruce
Attorney, Agent, or Firm—Richard J. Birch

[57]   ABSTRACT

This invention relates to the automatic determination of beam parameters and other criteria to determine a dose plan of radiation on a target volume. The method involves determination of geometric and other radiation involvement criteria, with search of a phase space on the incoming direction of the irradiation beam ports. The evaluation of the goodness of fit, based on parameter thresholds and other considerations, makes it possible to search on the entire phase space of possible beam directions towards the target volume so as to improve the treatment planning dosimetry. The invention applies to circular or non-circular collimator shapes, and can be illustrated by use with a linear accelerator (LINAC) as a means for X-ray delivery to a target volume such as a tumor within a patient's body.

1 Claim, 1 Drawing Sheet

AUTOMATIC PLANNING FOR RADIATION DOSIMETRY

BACKGROUND OF THE INVENTION

The method of radiation therapy using X-ray beams and ionizing particle beams has been known now for several decades. This method is used typically to treat malignant or other tumors or maladies within the body. Most recently the advent of stereotactic radiosurgery and stereotactic radiotherapy has been invoked with X-ray beams and charge particle beams to focally irradiate target volumes within the body based on three-dimensional calculation of the target volume from imaging and three-dimensional dosimetry using incoming beams from multiple directions towards the target volume. This is illustrated by the brochures from Radionics, Inc. on their stereotactic radiosurgery system.

Typical treatment planning systems, such as XKnife from Radionics, enable the phase space of possible X-ray beam angles to be manipulated on a computer workstation and visualized graphically. In addition, the selection of collimator sizes and target isocenter, which is a convergent point for incoming beams, can be adjusted. Once a multiple set of beams has been set up to a specified and calculated target volume, the dosimetry of radiation associated with these beams can be thereafter calculated and the dose at each point within the volume, including points in the tumor target volume as well as points in neighboring normal tissue, can be determined. Typically, such plans seek to get the maximum radiation and maximum surface dose homogeneity on a target volume, while at the same time minimizing the dose to critical volumes and structures in the vicinity of the aberrant target volume. Radiation-sensitive structures such as the brain stem, optic globes, and nerves are particularly important to take into account in such plans. Reduction of the geometric intersection of the beams from acceptable input directions to these critical structures is part of the plan. Typically, these plans are done by physicists and radiation therapists who have skill in being able to select the appropriate beam phase space of incoming angles, and thereby set up the plan as quickly as possible. Very involved plans where critical structures surround the tumor volume are much more difficult and can require significant amount of human labor, even with a high-powered computer graphic workstation.

Thus, it is desirable to be able to automate the selection of phase space of incoming beam directions to produce in an automatic fashion a dosimetry plan and plan of incoming directions to both maximize the effective dose on a target volume and minimize the effect of radiation on critical or normal structures in the vicinity of the target volume. It is one of the objectives of this patent application to describe a method whereby such an automatic planning system can be set down. The use of geometric constraints during a computation of the treatment plan is invoked, and the use of threshold dosimetric criteria involving the coverage of the target volume and the involvement of critical surrounding structures is used to search in the phase space and optimize the plan automatically.

It is the objective of this patent application also to describe a computational methodology that can be exercised on a computer workstation whereby such an automatic dosimetry plan can be utilized.

DESCRIPTION OF THE INVENTION

The invention relates to any radiation delivery system, whether it be X-rays from a linear accelerator, cobalt unit, or other X-ray delivery system, or charged particle radiation beams from such as electrons, protons, heavy ions, etc. Those skilled in the art can make variations of the embodiments which are described here, and it is understood that such variations will be included within the scope of the present invention. For the purpose of illustration, the embodiments of the invention involving X-ray beams from a linear accelerator (LINAC) will be described.

Figure 1:
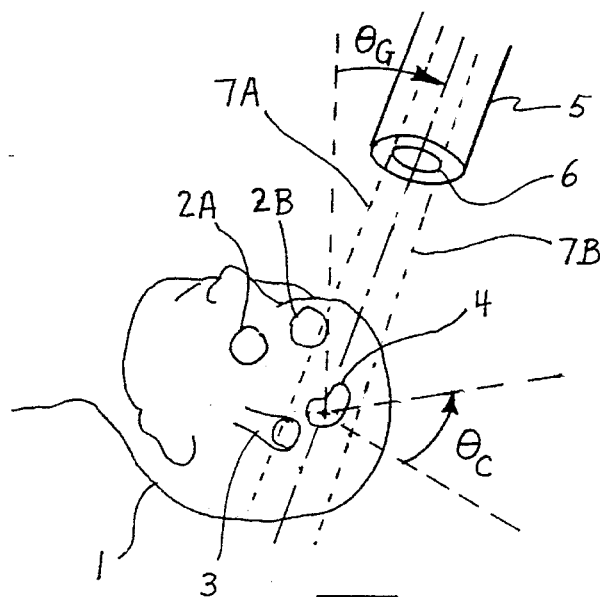
FIG. 1 shows the geometry of a radiation beam relative to a patient to be irradiated.

As an illustration of the present invention, referring to FIG. 1, a collimator housing 5 which holds a beam collimator with aperture 6 is shown relative to a patient's body, in this case the head of the patient 1. Within the head is a target volume 4, which may be an irregularly shaped tumor. In addition, for illustration are shown critical anatomical objects such as the eye globes 2A and 2B and the brain stem 3. The object of irradiation of X-ray beams from a LINAC which is attached to the collimator 5 is to collimate the beams so that they hit the target volume and do not hit the critical objects. By changing the angle of the collimator 5 according to the two polar angles $\theta_C$ and $\theta_G$ varying angular approaches of the X-ray beam can be achieved. These angles may correspond respectively to the couch angle and the gantry angle of a linear accelerator. The description of such couch and gantry angles are commonplace in the field of radiation therapy using LINACs.

Typically, dosimetry is planned using a treatment planning computer with appropriate software. This makes use of input of the beam parameters and characteristics for the beam profile, illustrated by the margins 7A and 7B, corresponding to a collimator 6, and relative to the patient's anatomy. Cognizance of the volume 4 and other critical structures such as 3 and the external surface of the head 1 must be taken into account. Appropriate depth dose, beam characteristics such as off-axis beam intensity and depth dose as a function of distance into the tissue must all be taken into account in characteristics of the beam. In the planning phase, the dose is calculated using a multiplicity of possible ports corresponding to angles $\theta_G$ and $\theta_C$. In some cases, continuous arcs are inputted, and in other cases discrete arc directions. In any case, a human being, typically a physicist, inputs the geometry and the possible arc angles as well as collimator geometries to do a manual computation of optimization of dose. A criterion of proper dosimetry may involve the degree of homogeneity of the dose on the surface and volume of the target volume 4, as well as the degree of non-involvement or minimization of radiation in critical structures such as the brain stem 3. This is a typically a laborious process, requires trial and error of the various beam phase space angles, and analysis of the dosimetry on target and other objects using such methods as dose volume histograms from a tissue surface inhomogeneity, degree of dose on neighboring critical objects, etc. Such methodologies are commonly known in the field of treatment planning, and reference to them can be found in the brochures and manuals for XKnife Stereotactic Radiosurgery System of Radionics.

Figure 2:
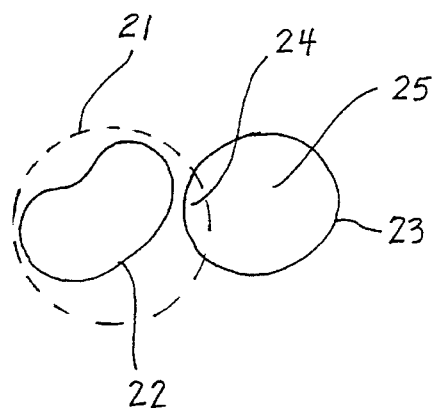
FIG. 2 shows a beam's-eye view relative to target volume and a critical structure.

The present invention illustrates a method whereby an automatic computation can be done of dosimetry assuming an initial phase space, and a convergence to an optical phase space can be approached using coverage and involvement criteria that can be set down in the computer code by the operator initially. Examples of such coverage and involvement criteria can be seen in FIG. 2. Here the dashed circle 21 illustrates the profile in the so-called beam's-eye view, that is, as viewed from a direction looking down the principal axis of the beam 7A and 7B of FIG. 1. Thus, for example, if the collimator 6 is circular, then the profile 21 would also be a circle. Equally illustrative would be collimator shapes which are non-circular. One can see the outline from the beam's-eye view of the tumor volume 22, and also the outline of the critical structure, for example, an eye globe 23. One can see that the coverage of the beam profile 21 encompasses the tumor volume or target volume 22, but also eclipses to a certain degree the critical structure 23. One could set down coverage or involvement criteria in such a figure by quantifying the percentage area or volume, or some weight function of these factors, of intersection of the critical volume 23. For example, the intersection area 24 could be compared to the non-intersected area 25, or compared to the total surface projected area 23. In the same way, the degree of coverage of the tumor volume might be set down as the ratio of tumor volume coverage to non-tumor-volume coverage in such a beam's-eye view figure. Thereby, coverage parameters, possibly indicated by area ratios of coverage versus non-coverage can be laid down for each of the anatomical objects in the tumor in the region of the body encompassed by the beam phase space.

Figure 3:
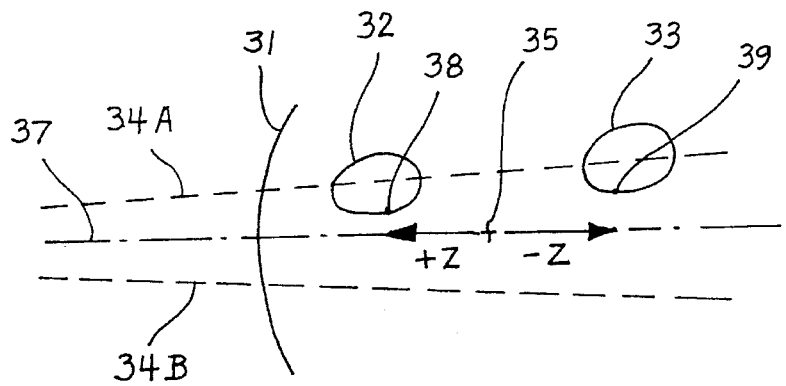
FIG. 3 shows a transverse sectional view showing two target sites relative to the external surface of the patient.

Other criteria for radiation coverage might be an involvement calculation. This can be illustrated in FIG. 3. The profile outer margins of the beam are illustrated by dashed lines 34A and 34B. They penetrate the body through the external surface 31 and intercept structures 32 and 33, which are at different depths within the body. The point 35 may represent the isocenter, that is, the common point of rotation of all the beam directions as illustrated by the beam axis 37. The distance from the isocenter 35 to any position along the beam axis, such as the point 38, may be illustrated by the on-axis distance +Z. Similarly, to any point on the structure 33, such as point 39, would be illustrated by −Z, since it is deeper into the body. One can define an involvement parameter I to indicate the amount of beam intensity or dose on the object 32 or 33 by the following formula:

$$I = 1/n \sum_i W_i \text{ and,}$$

$$W_i = e^{\mu Z_i} D(D - Z_i)^{-2}$$

where there are n random points on any given object such as 32, illustrated by the index i, and the factor $W_i$ is a measure of the amount of radiation relative to isocenter, which is a product of the attenuation factor $e^{\mu Z_i}$, where $\mu$ is the beam attenuation parameter, $Z_i$ is the distance from the i'th point from isocenter 35, and a geometric factor in which D is the distance from the source to the isocenter 35, where the source is the source of X radiation from the linear accelerator, giving rise to the beam outlines 34A and 34B. It can be seen that for the object 32 the involvement I is greater than the involvement for the object 33, since object 32 is closer to the beam where the intensity is greater and the beam is not diverged as much as in the region of object 33, which is farther away from the source. Other types of formulations of the degree of beam intensity on a given object as a function of distance from the source and as a function of tissue penetration to that object can be formulated by those skilled in the art. These considerations illustrate means of making geometric involvement calculations of target and non-target objects which can be put into a three-dimensional data base in a dose planning computer workstation. These involvement or coverage criteria can be used to assess and/or restrict the phase space of available beam entry positions into the body. The involvement factors or coverage factors for the target volume could be different than for the volumes associated with critical structures or other anatomical structures. In addition, other criteria could be invoked which have to do with the quality of a dose plan. Examples of these might be the overlap of beams from different elements of phase space. Overlap of beams or intersection of beams or degeneracy of beams can give rise to hot spots or over-radiation regions on the tissue, which is undesirable. These can be represented by overlap factors of beams easily within the computer data base associated with the phase space, target, and anatomical volumes. Another criterion which can be used is total surface dose inhomogeneity which is related to the degree of non-uniformity of the dose on the surface of the target volume, for example. Furthermore, criteria of the length of the arcs of the beams in the phase space, if continuous arc beams are used or discrete approximation to arc beams are used, could be invoked as to the limitations or constraints on the entire phase space of a planned treatment calculation. The degree of depth penetration within the tissue could be used to discriminate or favor probablistically one beam phase space over another. The longer depths of penetration may be less desirable than more short or shallow depths of penetration, and waiting factors as well as quality criteria could be associated with such parameters.

As an illustration of the way that these parameters can be used to automatically compute a dose plan in a computer workstation, we could take the process of so-called simulated annealing to optimize a plan based on criteria or predetermined parameters selected by the dose planner related to these involvement, coverage, beam arc, inhomogeneity, or other specifications of the plan. One could, for example, set acceptance levels or thresholds for each of these criteria and then search on the phase space of beam arcs and beam collimator cross sections so as to optimize a plan with the constraint associated with these thresholds or acceptance levels for the various beam parameters. One could initiate by a random initial selection of beam phase space a search within the computer which could then make movements within the phase space of the beam parameters and put a quality value on any given dose plan which results. Such a quality value could be, for example, the cost function weighted by the values of the parameters of specifications cited above, such as involvement, coverage, surface dose inhomogeneity, depth penetration, etc. The computer could make a move in phase space by moving an increment of one element of phase space to another part of the phase space map while staying in certain physical constraints of the phase space associated with the actual beam position relative to the patient, or the gantry relative to the couch in the case of the LINAC. The cost functions could be recalculated to see if the dose plan was improved or not improved based on the cost function. The simulated annealing process would continue by stepping such phase space moves and looking at the incremental improvement or lack of improvement based on this cost function criteria. The simulated annealing process is known in the computational optimization field and could be used in this case to help in the automated dose optimization routine which is specified in this invention. Multiple target volumes could be used in the same way, as well as multiple isocenter dose plans. Among the criteria that could be used to constrain or drive such a simulated annealing is the maximization of involvement of the tumor volume as compared to the minimization of the involvement or coverage of the anatomical objects which are critical. There are many other algorithms or mathematical criteria by which the goodness of fit or the goodness of coverage of target versus other volumes could be quantified. These approaches are known to those skilled in the art. The elimination of angles of beam approach and phase space can also be constrained by clinical considerations related to the patient's anatomy. The calculation of involvement and the restriction of the phase space accordingly may be done by looking at set points established by the operator or pre-established by other criteria on the involvement and coverage factors and constraining the phase space to only be allowed to satisfy an inequality of these involvement factors, either less or above the set point. Other absolute criteria could be invoked to constrain further the phase space. Gantry angles which are opposed by approximately 180° or couch angles which are opposed by approximately 180° give beam overlap or redundancy, and thus the phase space can be constrained or reduced automatically by eliminating such redundant or degenerate beam approaches. These criteria might be considered absolute criteria. The optimization criteria might be distinguished from these by the set point parameters on the involvement, coverage, surface dose inhomogeneity, separation of beam criteria, depth, length, and arc length parameters referred to above. A simulated annealing calculation could be done on the beam phase space, taking all of these parameters and other parameters which might be invoked by those skilled in the art into account as constraints on the calculations. The constraints could give rise to quality factors or mathematical criteria which allow an optimization or driving of the calculation towards a better dose plan, or an optimized dose plan, or a dose plan which falls within certain physical criteria. These all could be considered as automatic dose planning calculations and fall within the method claimed by this invention. The use of beams which are circular or irregularly shaped could be invoked. The use of phase space associated with non-LINAC type devices such as proton beams or multi-port fixed cobalt source machines could be invoked for this purpose. The optimization may not be a complete optimization and search of phase space but only a reduction of phase space automatically so as to enable an operator to carry on from that point with manual intercession to approach a plan which would thereafter be acceptable based on other considerations.

Having described a typical embodiment of the present invention, it is important to note that the example given above is not meant to limit the scope of this invention, but merely to illustrate one possible use. Having thereby described the invention, what we claim by U.S. Letters Patent are the following.

We claim:

1. A method of automatic dose calculation of radiation dose on a target volume within the body of a patient, including a dose calucation of the radiation dose and an automatic search on said radiation dose, said dose calculation comprising the steps of:

(a) irradiating the patient with a radiation beam of radiation from a radiation delivery apparatus to represent said target volume and the position of other anatomical objects in said body in a computer data base in a computer means, and represent the beam characteristics of the radiation beam of radiation from the radiation delivery apparatus with respect to said target volume and said anatomical objects as a function of the beam phase space of possible approaches of said radiation beam onto said target volume and said anatomical objects;

(b) for each element of said beam phase space, calculating a target geometric involvement factor and an anatomical object geometric involvement factor related to the geometric interception of said radiation beam on said target volume and said anatomical object respectively;

(c) determining a target acceptance criteria for said target geometric involvement factor and an anatomical object acceptance criteria for said anatomical object which relates to the acceptability of said radiation dose on said target volume and said anatomical objects;

(d) computer searching by said computer means on said beam phase space so as to automically determine an acceptable sub-portion of said beam phase space which satisifies said target acceptance criteria and said anatomical object acceptance criteria simultaneously so as to thereby enable automatic optimization of said radiation dose on said target volume within the constraint of said target acceptance criteria and said anatomical object acceptance criteria.

* * * * *